(12) United States Patent
Miller et al.

(10) Patent No.: US 11,191,548 B2
(45) Date of Patent: Dec. 7, 2021

(54) METHOD AND APPARATUS FOR INTRALUMINALLY OCCLUDING HOLLOW OR TUBULAR BODY STRUCTURES

(71) Applicant: Amsel Medical Corporation, Cambridge, MA (US)

(72) Inventors: Arnold Miller, Cambridge, MA (US); Raanan Miller, Cambridge, MA (US)

(73) Assignee: AMSEL MEDICAL CORPORATION, Cambridge, MA (US)

( * ) Notice: Subject to any disclaimer, the term of this patent is extended or adjusted under 35 U.S.C. 154(b) by 92 days.

(21) Appl. No.: 16/573,600

(22) Filed: Sep. 17, 2019

(65) Prior Publication Data
US 2020/0085443 A1     Mar. 19, 2020

Related U.S. Application Data

(60) Provisional application No. 62/732,875, filed on Sep. 18, 2018.

(51) Int. Cl.
| | | |
|---|---|---|
| *A61B 17/128* | (2006.01) | |
| *A61B 17/122* | (2006.01) | |
| *A61B 17/34* | (2006.01) | |
| *A61B 17/00* | (2006.01) | |

(52) U.S. Cl.
CPC ........ *A61B 17/1285* (2013.01); *A61B 17/122* (2013.01); *A61B 17/3478* (2013.01); *A61B 2017/00278* (2013.01); *A61B 2017/00584* (2013.01); *A61B 2017/00592* (2013.01); *A61B 2017/00606* (2013.01); *A61B 2017/00619* (2013.01); *A61B 2017/00623* (2013.01); *A61B 2017/00632* (2013.01); *A61B 2017/00871* (2013.01)

(58) Field of Classification Search
CPC . A61B 17/0057; A61B 17/122; A61B 17/128; A61B 17/1285; A61B 2017/00575; A61B 2017/00584; A61B 2017/00592; A61B 2017/00606; A61B 2017/00615; A61B 2017/00619; A61B 2017/00623; A61B 2017/00632
See application file for complete search history.

(56) References Cited

U.S. PATENT DOCUMENTS

| | | | | |
|---|---|---|---|---|
| 5,865,791 | A * | 2/1999 | Whayne | A61B 17/00234 604/500 |
| 6,071,292 | A * | 6/2000 | Makower | A61B 17/0401 606/139 |
| 6,231,561 | B1 * | 5/2001 | Frazier | A61B 17/0401 604/500 |
| 7,144,363 | B2 * | 12/2006 | Pai | A61B 17/00234 600/16 |
| 9,936,955 | B2 * | 4/2018 | Miller | A61B 17/1214 |
| 10,076,339 | B2 * | 9/2018 | Miller | A61B 17/12009 |
| 10,398,445 | B2 * | 9/2019 | Miller | A61B 17/122 |

(Continued)

*Primary Examiner* — Ryan J. Severson
(74) *Attorney, Agent, or Firm* — Bookstein IP Law

(57) ABSTRACT

Catheter-based devices and methods for endoluminally accessing and occluding hollow anatomical structures are disclosed. Occlusion clips are contained in one or more needles that pierce opposing walls of the anatomical structure to deploy the clips externally of the structure. The clips then are drawn together to press the opposing anatomical walls together.

18 Claims, 23 Drawing Sheets

(56) References Cited

U.S. PATENT DOCUMENTS

| | | | |
|---|---|---|---|
| 10,687,805 B2* | 6/2020 | Miller | A61B 17/072 |
| 10,702,274 B2* | 7/2020 | Groothuis | A61B 17/0401 |
| 10,820,895 B2* | 11/2020 | Miller | A61B 17/0057 |
| 2003/0078465 A1* | 4/2003 | Pai | A61B 17/0401 600/16 |
| 2005/0277966 A1* | 12/2005 | Ewers | A61B 17/0401 606/153 |
| 2007/0043344 A1* | 2/2007 | McAuley | A61N 7/02 606/27 |
| 2007/0083232 A1* | 4/2007 | Lee | A61B 17/12122 606/213 |
| 2007/0144539 A1* | 6/2007 | van der Burg | A61B 18/1477 128/897 |
| 2007/0265658 A1* | 11/2007 | Nelson | A61F 2/2487 606/213 |
| 2007/0276437 A1* | 11/2007 | Call | A61B 17/0487 606/232 |
| 2008/0033241 A1* | 2/2008 | Peh | A61B 1/3137 600/109 |
| 2011/0046622 A1* | 2/2011 | McAuley | A61N 7/02 606/41 |
| 2011/0301595 A1* | 12/2011 | McAuley | A61B 17/12122 606/41 |
| 2012/0116269 A1* | 5/2012 | McAuley | A61B 17/12122 601/2 |
| 2012/0283758 A1* | 11/2012 | Miller | A61B 17/12031 606/158 |
| 2013/0046331 A1* | 2/2013 | Christensen | A61B 17/12036 606/200 |
| 2014/0243857 A1* | 8/2014 | Miller | A61B 17/12109 606/142 |
| 2015/0173765 A1* | 6/2015 | Miller | A61B 17/12 606/49 |
| 2015/0290428 A1* | 10/2015 | Tkebuchava | A61M 25/003 600/486 |
| 2017/0340329 A1* | 11/2017 | Groothuis | A61B 17/0401 |
| 2018/0021044 A1* | 1/2018 | Miller | A61B 17/12031 606/142 |
| 2018/0214270 A1* | 8/2018 | Subramanian | A61F 2/246 |
| 2018/0361118 A1* | 12/2018 | Cully | A61B 17/0469 |
| 2020/0085443 A1* | 3/2020 | Miller | A61B 17/3478 |

* cited by examiner

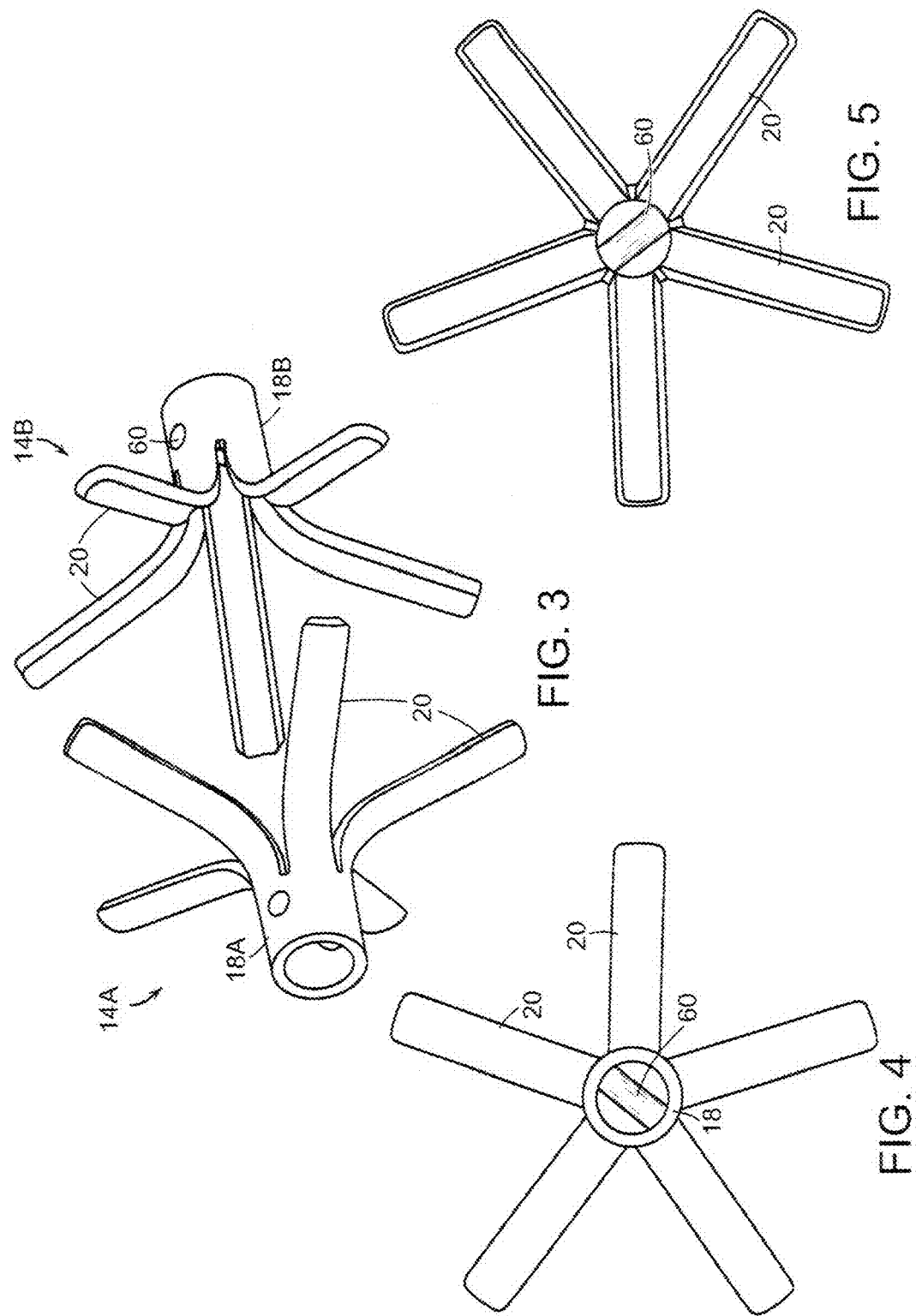

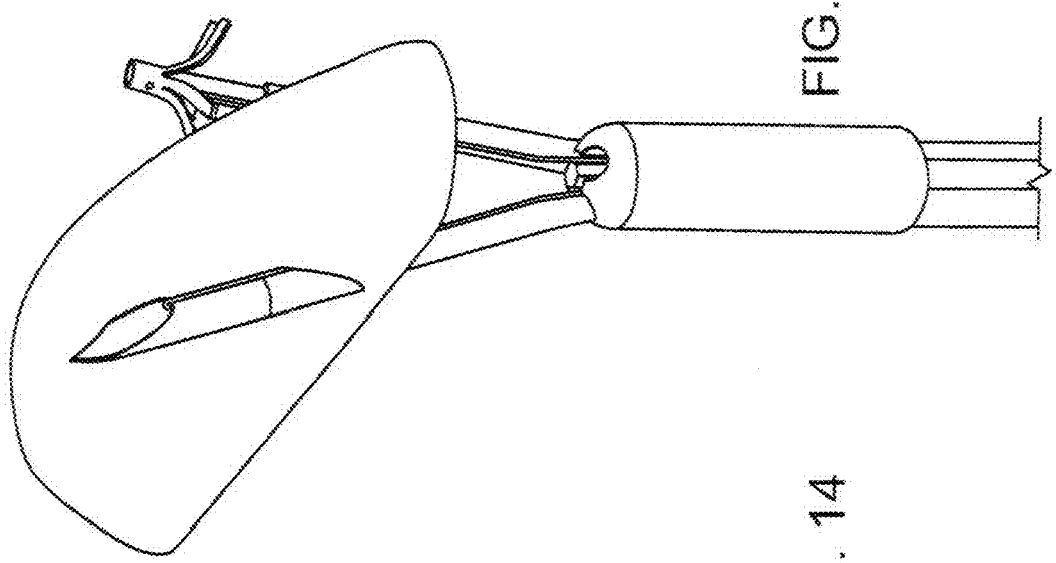
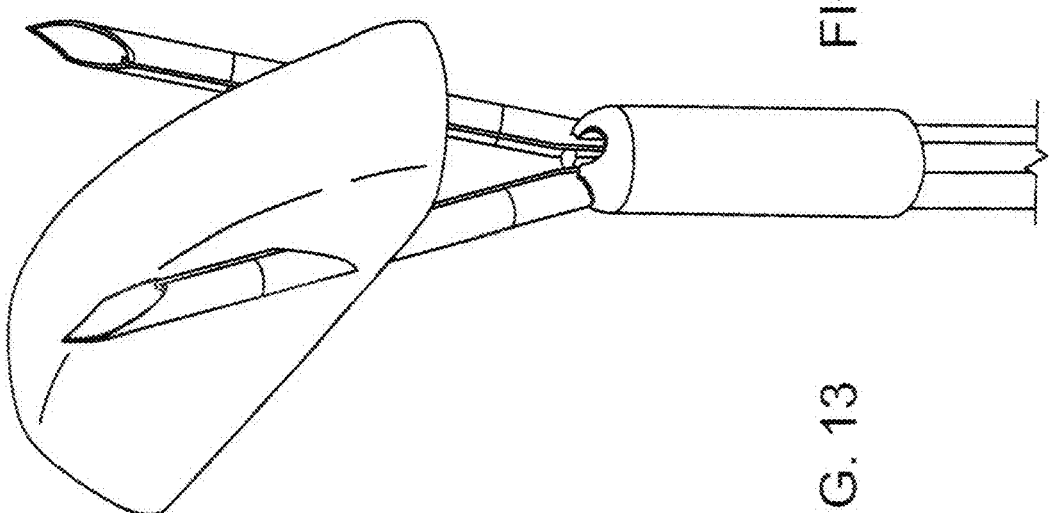
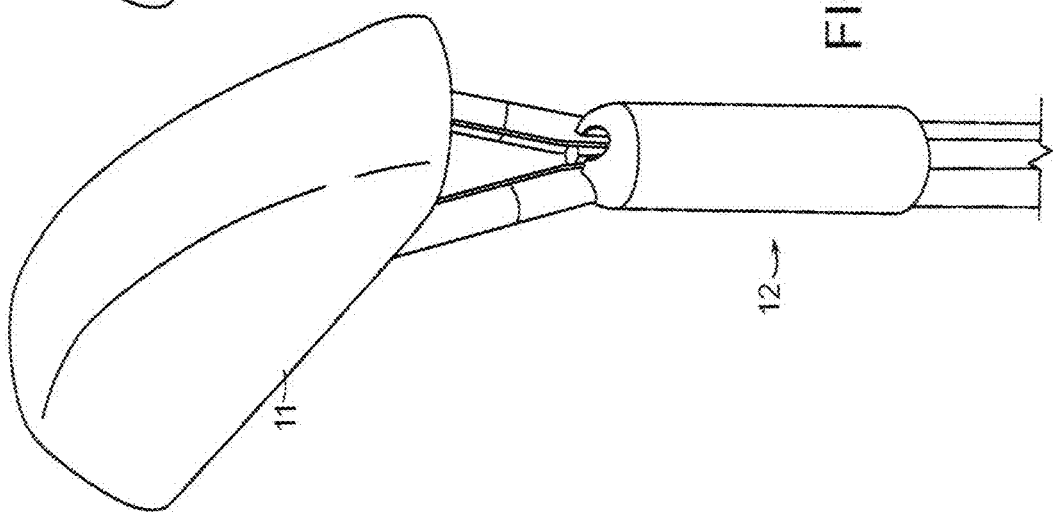

US 11,191,548 B2

METHOD AND APPARATUS FOR INTRALUMINALLY OCCLUDING HOLLOW OR TUBULAR BODY STRUCTURES

RELATED APPLICATIONS

This application claims benefit of provisional application 62/732,875, filed Sep. 18, 2018 and is a continuation in part of prior patent application Ser. No. 16/450,931, filed Jun. 24, 2019, the disclosures of which are incorporated by reference herein, in their entireties.

FIELD

The invention relates to intraluminal methods and devices for partially or fully occluding hollow or tubular anatomical structures.

BACKGROUND

Many surgical procedures are performed to reduce or close off the interior volume of a hollow body organ or vessel. In one such example, conditions exist in which an appendage of the left atrium of a heart may not function effectively and may result in stagnation of blood that, in turn, may cause the formation of blood clots that could enter into the blood stream with the potential for stroke or myocardial infarction. It may be desirable in such cases to isolate the left atrial appendage (LAA) in an attempt to reduce or eliminate the risk of blood clot formation.

Various approaches to isolate the LAA have been employed, some of which are relatively invasive and involve open chest surgery. One approach is to close the ostium of the LAA, as with a row of sutures to prevent blood flow into or out of the appendage. Another approach is to surgically remove the atrial appendage after first closing the ostium with sutures. It would be desirable to provide less invasive surgical devices and techniques by which the LAA, as well as other hollow or tubular anatomical structures or selective parts of these structures, such as the stomach or bowel, might be isolated or occluded, for example, as an alternative to a gastric sleeve.

SUMMARY

The invention provides devices and techniques by which the interior of hollow or tubular anatomical structures may be accessed through natural lumens leading to the anatomical structure. The device includes a catheter that is introduced and advanced intraluminally to the interior of the organ at the treatment site. As used herein for convenience, the term "catheter" is intended to include any elongate, tubular device conventionally designated as such, as well as endoscopes or the working channel of an endoscope and the like, adapted to be passed through one or more anatomical lumens, such as a blood vessel, esophagus, stomach, bowel, intestines or other luminal or hollow organs.

The catheter carries a pair of hollow needles, each of which contains an occlusion clip in a low-profile configuration. The clips, when ejected from the ends of the needles, self-expand to an enlarged configuration. The clips are connected to each other by an arrangement of one or two cords that, after the clips have been passed through opposing walls of the hollow structure and are deployed to their expanded configuration externally of the organ, the cord or cords can be manipulated to draw the clips together so that the walls of the structure disposed between the clips can be brought together. Each cord has a head end that is securely attached to a clip and a trailing tail end from which it can be manipulated.

When the distal end of the catheter has been advanced to the treatment site, the needles are extended beyond the distal end of the catheter to and through opposing walls of the hollow organ so that the needles pierce the walls at opposite sides of the organ. With the distal tips of the needle outside of the organ, the clips are urged out of the needles and self-expand externally of the organ. The needles then are withdrawn and the tail end(s) of the cord(s) then are manipulated to pull the clips toward each other until the clips have drawn the opposing walls of the organ together. The device includes arrangements for securing the cords to maintain the clips in their tissue-clamping configuration to prevent separation of the clips and clamped tissue. The tails of the cords then can be severed leaving the clips in place. The procedure may be repeated at an adjacent portion of the organ until the organ has been isolated or otherwise modified, as desired.

In another embodiment of the invention, the two clips can be contained in tandem within a single needle, and deployed sequentially out of the lumen of the needle or catheter.

In this embodiment the needle first pierces one wall of the tubular structure or hollow organ and the first clip is deployed on the outside of the structure. The needle is then retracted back into the tubular structure or hollow organ and repositioned so that it can be re-advanced to pierce a second wall or another region of the tubular structure. The second clip is then is deployed out of the needle and is expanded externally of the tubular structure or hollow organ. Then, with both clips located externally of the tubular or hollow structure, the two clips are pulled together, clamping the tissue walls between them and collapsing or distorting the lumen of the tubular structure in a desired manner.

THE DRAWINGS

The advantages and objects of the invention will be appreciated more fully from the following description, with reference to the accompanying drawings in which FIG. 1 is a diagrammatic illustration of a portion of a hollow organ, such as a left atrial appendage, and a catheter after a pair of occlusion clips have been deployed and have clamped opposing walls of the organ;

FIG. 3 is an illustration of first and second clips of the invention;

FIG. 4 is an end view of the first clip as seen from the tubular end of the clip;

FIG. 5 is an end view of the first clip as seen from the leg end of the clip;

FIGS. 12-19 are illustrations of the sequence of operations in the use of the embodiment of FIGS. 1-11;

FIG. 27 is a diagrammatic slide showing an embodiment of the invention showing the delivery device which includes a stop to limit the protrusion distance of the needle or catheter on the outer side of the tubular structure or hollow organ to minimize any possible injury to surrounding structures. The structure may be made out of nitinol or stainless steel or a polymeric material that expands to limit the travel of the needle through the tissue.

Figure 28:
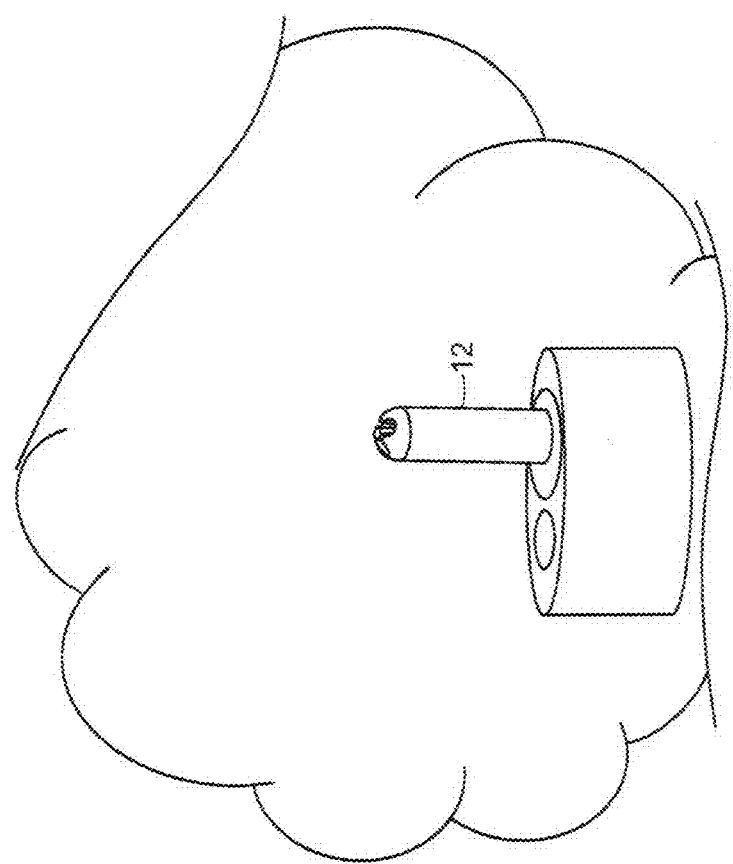

FIG. 28 shows an illustration of the invention delivered through the working channel of an endoscope into a hollow organ, in this illustration the stomach, for the purpose of selectively occluding certain regions of the stomach for example to create a gastric sleeve.

Figure 30:
Figure 31:
Figure 32A:
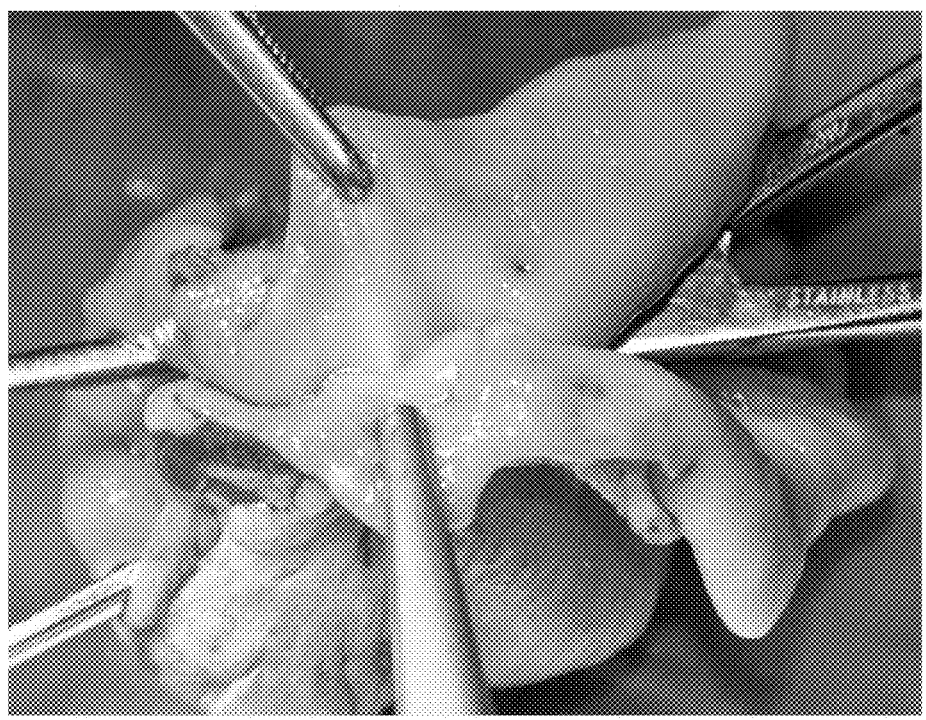
Figure 32B:
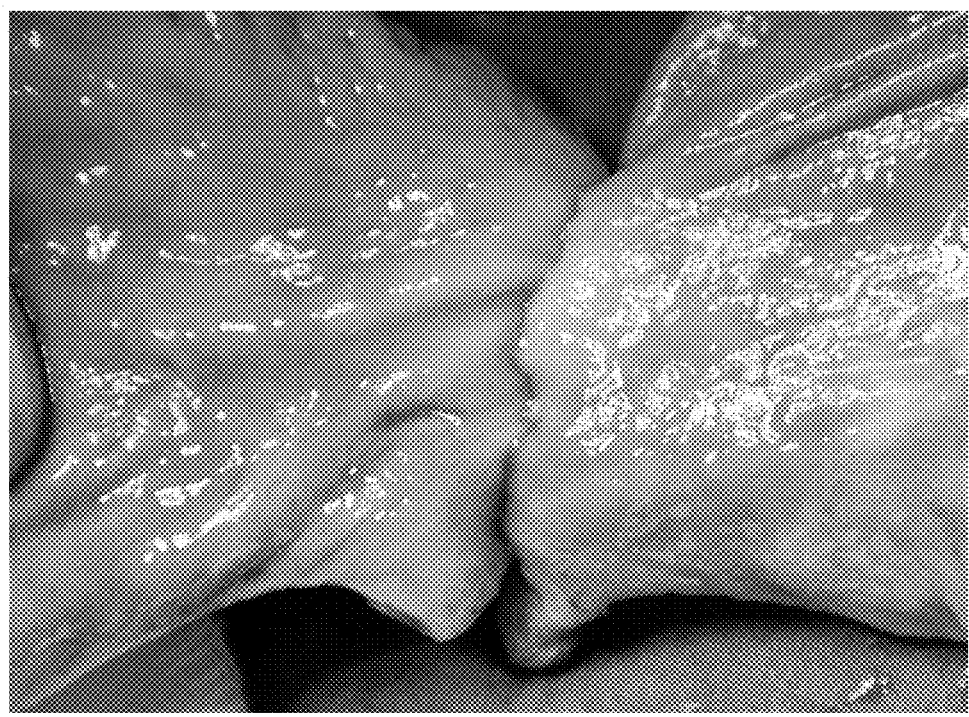

FIG. 29A-29D are diagrammatic illustrations depicting the sequence of steps in which a single needle having a plurality of clips arranged in series in the needle can be used in practicing the invention;

FIG. 30 is a photograph of the exterior of a stomach in which one of the clips has been deployed after having been passed through the wall of the stomach;

FIG. 31 is a photograph of the external surface of a stomach, accessed intraluminally, in which three pairs of occlusion clips have been deployed to draw opposing walls of the stomach together;

FIGS. 32a and 32b are photographs of a stomach that has been reduced in effective volume by applying occlusion clips to draw the inner surfaces of the stomach together. The photograph shows the inner surfaces of the stomach that has been surgically opened to show the manner in which the inner stomach surfaces are approximated.

ILLUSTRATIVE EMBODIMENTS

Figure 1:
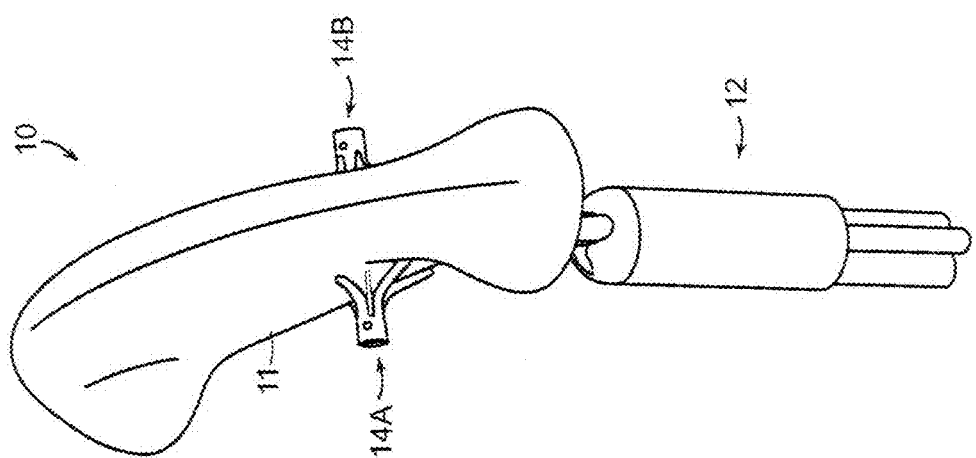

FIG. 1 illustrates, diagrammatically, a portion of a left atrial appendage (LAA) 10 and the distal end of a catheter 12 used to deliver occlusion clips 14A, 14B endoluminally, to clamp the opposing walls of the LAA together. FIG. 1 shows one pair of such clips clamping the opposed appendage walls. A number of pairs of such clips can be deployed along the atrial ostium to isolate the LAA so that blood does not flow into or out of the LAA.

Figure 2:
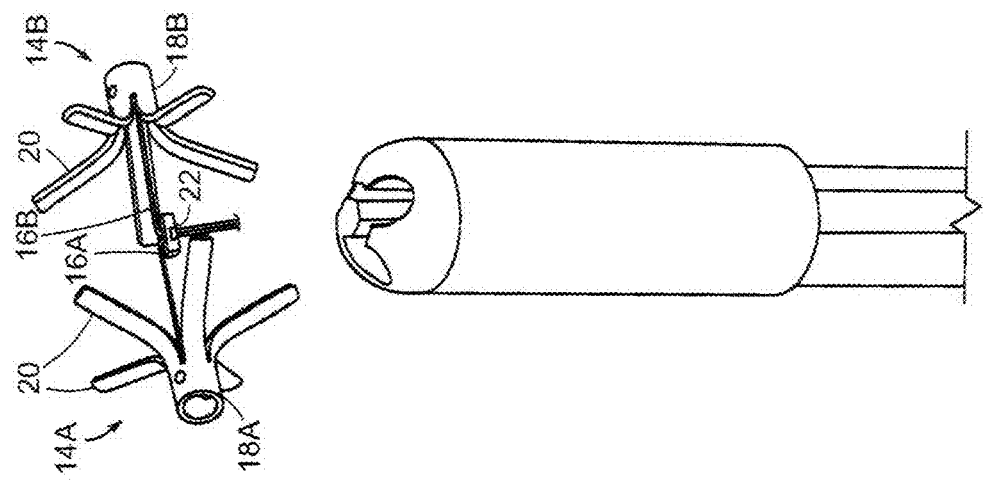
FIG. 2 illustrates, diagrammatically, the distal end of the catheter and a pair of clips 14A, 14B of one embodiment of the invention as they would be juxtaposed after deployment from the catheter, but with appendage tissue removed for clarity.

FIG. 2 illustrates, diagrammatically, the distal end of one embodiment of the catheter and a pair of clips 14A, 14B as they would be juxtaposed after deployment from the catheter, but with appendage tissue removed for clarity. Each of the clips 14A, 14B may be formed from a shape memory material, (e.g., Nitinol) to have a tubular base 18A, 18B, respectively, and a plurality of legs 20 that extend radially outward from the base 18 when a clip is in its expanded, unstressed condition (see, also, FIG. 3). The clips may be formed from a tube with a plurality of longitudinal slits formed from the midportion to the end of the tube to define the legs 20. The clips of the shape memory material may be formed, as by heat treatment, so that the legs will assume an expanded, radially extended configuration when released from a delivery needle. The legs 20 can be resiliently folded together to a low-profile, tubular configuration to be received in a delivery lumen of a needle or the like. In the embodiment shown in FIG. 2, each of the clips 14A, 14B is attached to what may be considered as the head end of elongate cords 16A, 16B, respectively, and the other, tailing ends of the cords 16A, 16B are passed through a cord lock 22. The cord lock 22 and cords 16A, 16B are arranged to permit the cords to pass through the cord lock only in a direction that will draw the clips toward the cord lock and each other. As used herein, the term "cord" is intended to include any elongate, flexible, thin member capable of functioning as described. Each clip may be considered as having a "tube end" defined by its tubular body 18 and a "leg end" which refers to the opposite end of the body from which the legs 20 extend.

Figure 6:
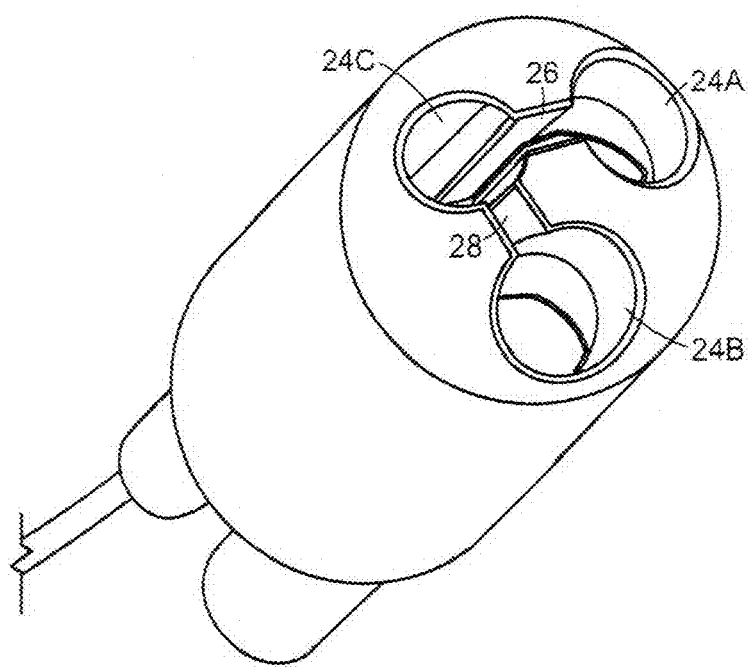
FIG. 6 is an illustration of the distal end of the catheter.

As shown in FIG. 6, the catheter 12 has three lumens 24A, 24B and 24C. Lumens 24A and 24B contain needles 30A and 30B (described below), and each needle contains one of the occlusion clips 14A, 14B in its unexpanded, low profile, delivery configuration. Lumen 24C contains the cord lock 22. Slots 26, 28 are formed between the cord lock lumen 24C and each of the needle lumens 24A, 24B to enable the cords 16A, 16B to extend from their respective clips out of the forwards ends of the needles through the slots 226, 28 into lumen 24C and to and through the cord lock 22, then out of the proximal end of the catheter.

Figure 7:
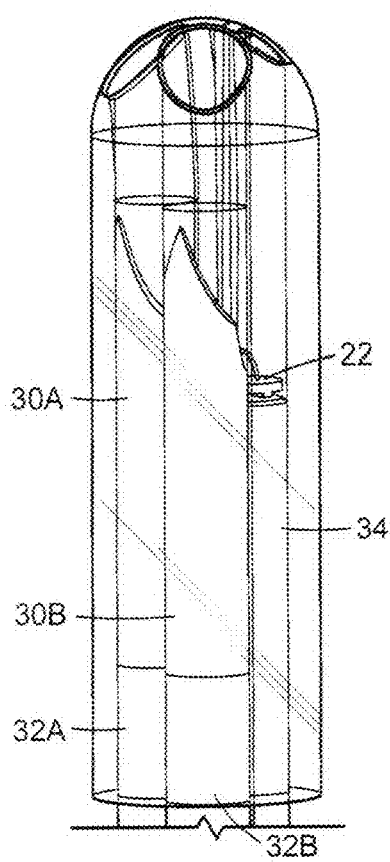
FIG. 7 is a diagrammatic illustration of the distal end of the catheter loaded with clip-containing needles, cord lock and pushing members.
Figure 8:
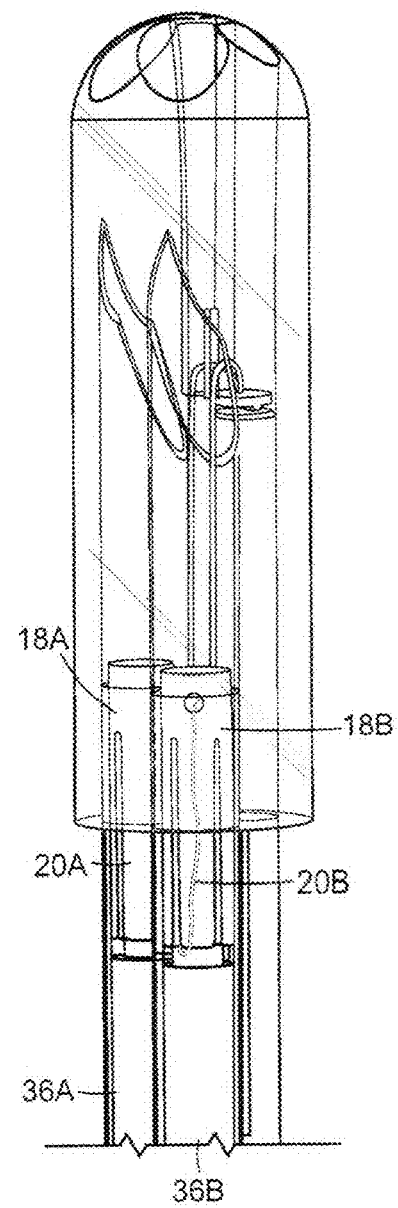
FIG. 8 illustrates, diagrammatically, the arrangement of the clips, clip push rods and needle push rods in the catheter.

FIGS. 7 and 8 are diagrammatic illustrations of the distal end of the catheter with needles 30A, 30B loaded in their respective lumens 24A, 24B. Each needle is associated with a needle control tube 32A, 32B that extends from the proximal end to the distal end of the catheter. The control tubes 32A, 32B are connected to their respective needles to push the needles out of or retract the needles into their respective catheter lumens 24A, 24B. A push tube 34 is contained in catheter lumen 24C and is controllable from the proximal end of the catheter. The push tube 34 contains the tails of the cords exiting from the cord lock 22, the cords extending beyond the proximal end of the catheter where they are accessible to the clinician. The push tube 34 can be advanced to push the cord lock 22 out of the distal end of the lumen 24C. As shown in FIG. 8 the catheter also includes clip push rods 36A, 36B that extend through the needle control tubes 32A, 32B and can be advanced through their respective needles. The clip push rods facilitate deployment of the clips out of their respective needles by pushing the clips or by maintaining the position of the clips as the needles are retracted.

Figure 9:
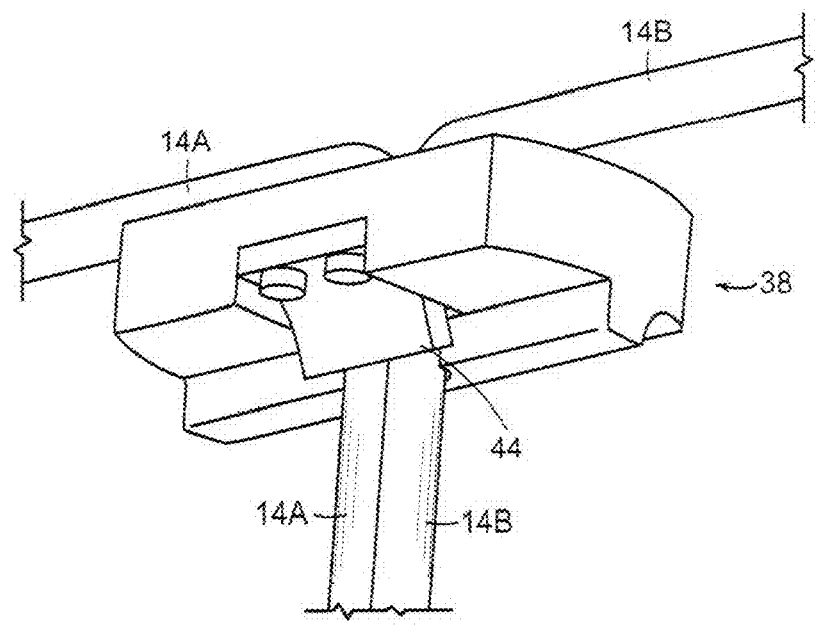
FIG. 9 is an isometric illustration of the cord lock.
Figure 10:
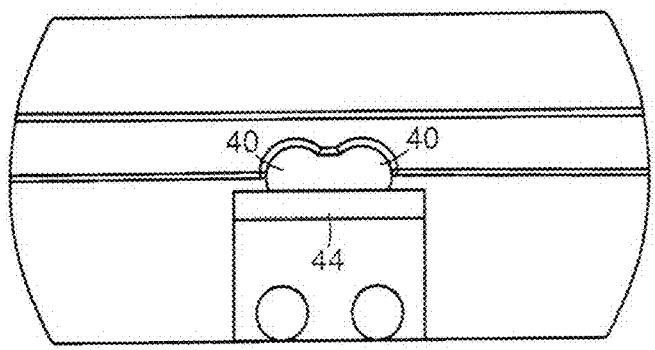
FIG. 10 is a bottom view of the cord lock.
Figure 11:
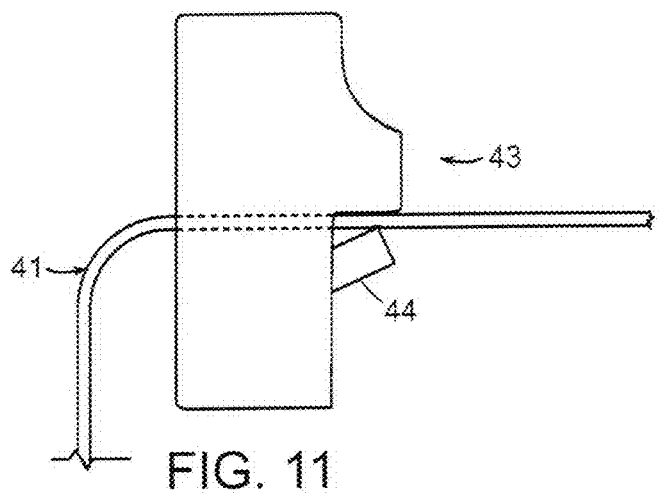
FIG. 11 is a side view of the cord lock.

FIGS. 9-11 illustrate, diagrammatically, an illustrative construction for the cord lock 22. In this embodiment the cord lock 22 includes a block 38 with one or two apertures 40 adapted to receive the cords 16A, 16B. Each aperture 40 may be considered as having an entry side 41 and an exit side 43. Secured to or formed integrally with the block 38 is a member 42 having an edge 44 that overlies the apertures 40 on the exit side 43 of the apertures. The edge 44 is arranged and oriented to engage the cords 14A, 14B as they emerge from the exit side 43 to allow the cords to pass through the apertures from the entry side to the exit side but not in the reverse direction. It should be understood that other arrangements for engaging and self-locking the cords may be employed. For example, one-way cords using beads, knots or barbs (e.g., zip-ties) or similar devices may be employed to achieve one-way movement of the cord(s)

Figure 12:
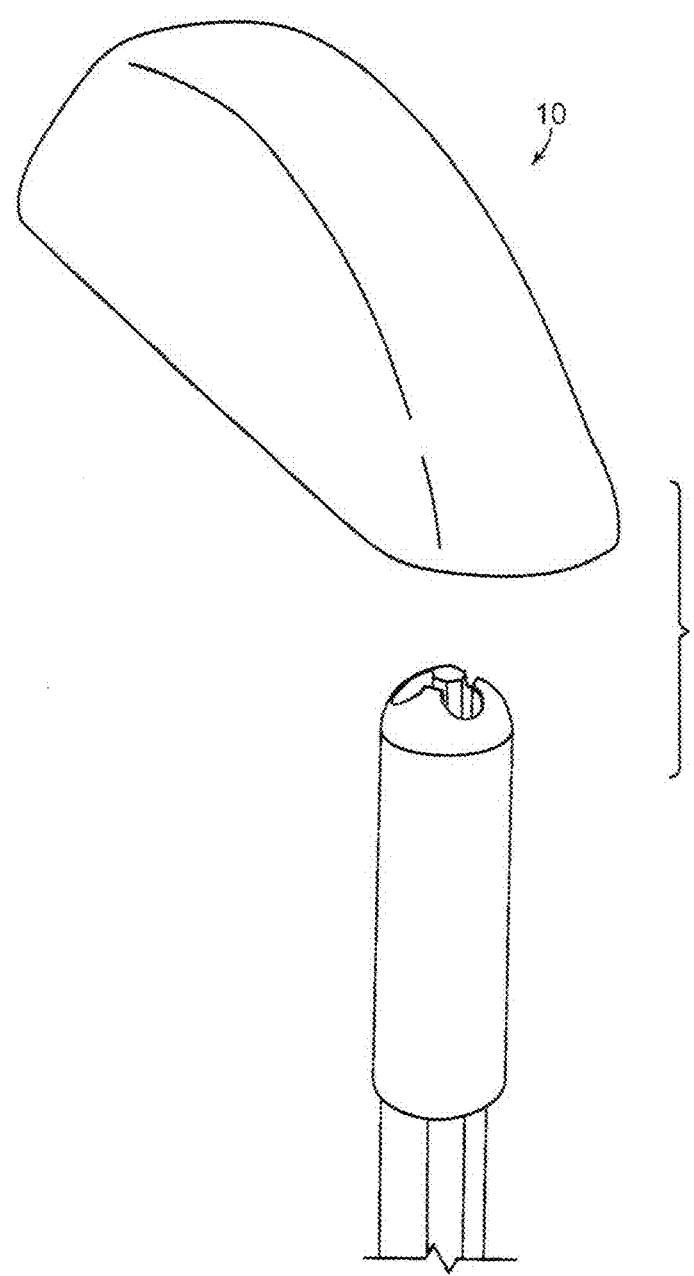

FIGS. 12-19 illustrate, diagrammatically a sequence of steps in the use of the device to access, intraluminally, and close off, for example, a left atrial appendage. The catheter is navigated through the patient's vasculature using well-known access techniques, to place the distal end of the catheter within the left atrium of the heart (FIG. 12). In the embodiment shown in FIG. 13 the distal ends of the lumens 24A, 24B of the catheter may be oriented to diverge so that the needles are oriented to be directed in diverging directions to direct the needles 30A, 30B at opposing walls of in the ostial region of the atrial appendage (FIG. 13).

Figure 18:
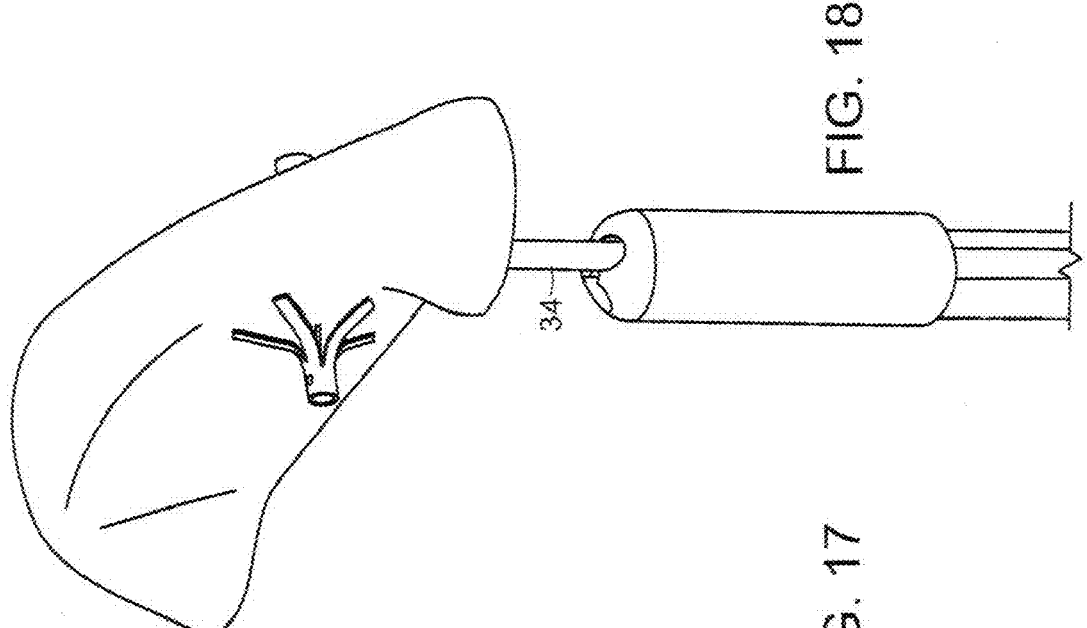
Figure 17:
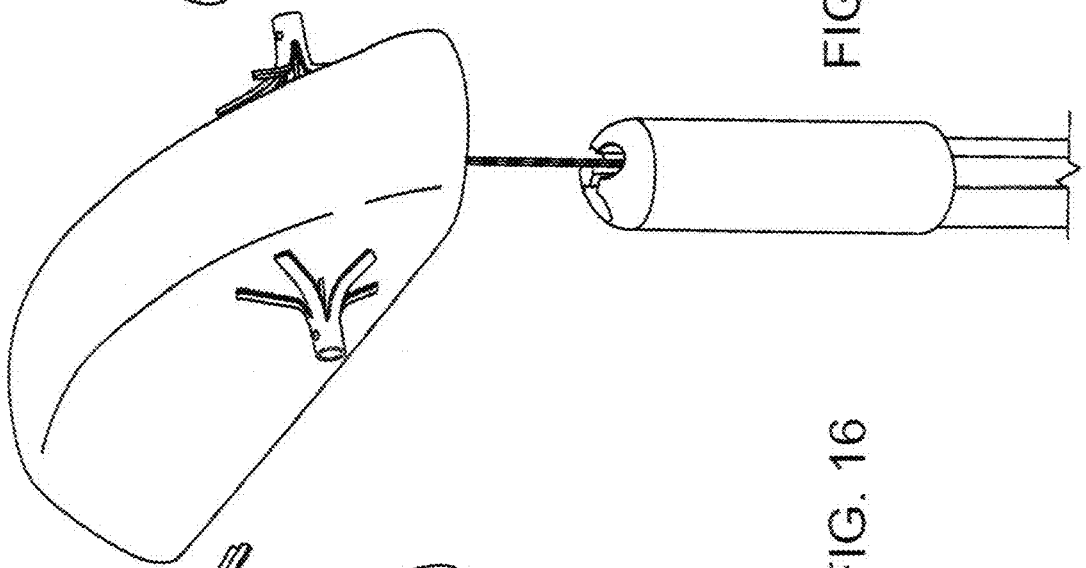
Figure 16:
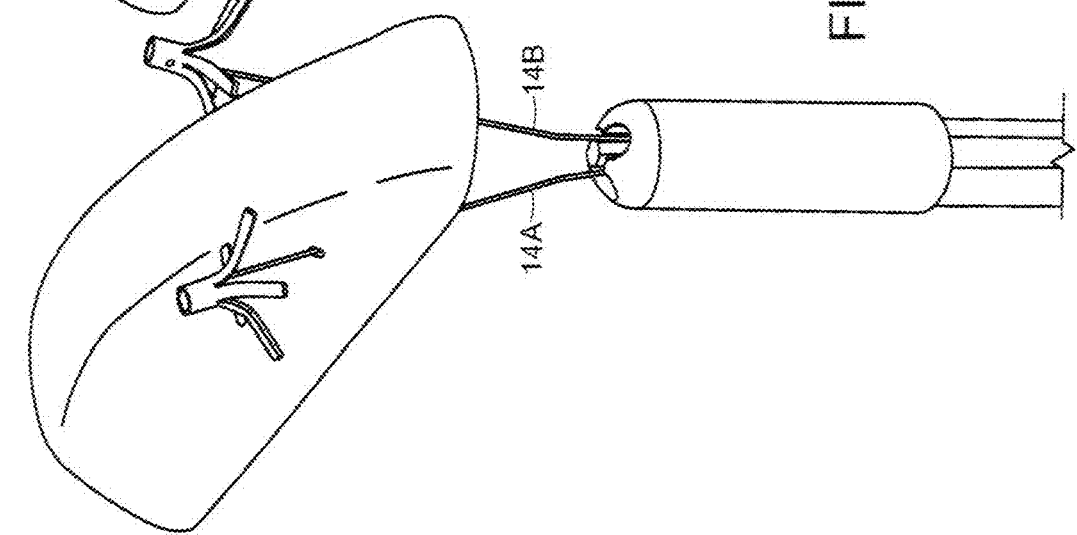
Figure 19:
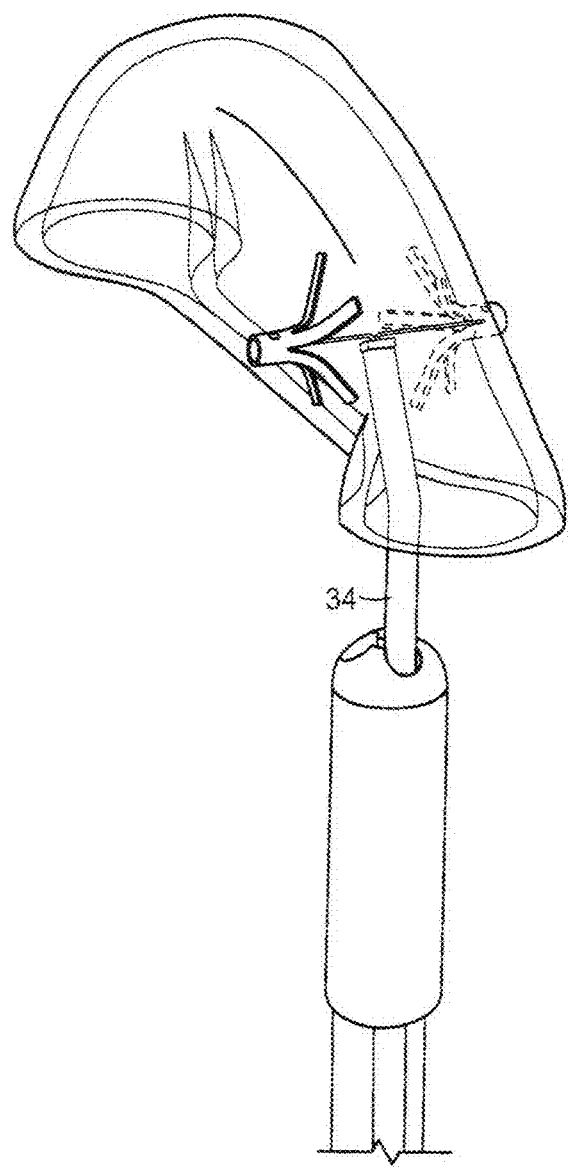

The needles then are extended by the needle control rods 32A, 32B to pierce opposing walls of the appendage (FIG. 14) and with the tips of the needles positioned externally of the appendage, the clips are pushed out of the needles by advancing the clip push rods 36A, 36B through the needles or by retracting the needles while maintaining the position of the push rods. The needles may be oriented and positioned to pierce the appendage walls in proximity to the ostium of the appendage. Upon release from the needles, the clips self-deploy to an expanded configuration with their legs extending radially (FIG. 15). With the clips expanded, the clip push rods 36A, 36B are retracted and the cord lock push tube 34 is advanced along the tails of the cords 14A, 14B to push the cord lock out of the lumen 24C (FIGS. 18, 18A). As the cord lock push tube is advanced over the cords 14A, 14B while holding the tails of the cords, the cord lock 38 advances over the cords to progressively draw the cords through the cord lock, thus drawing the clips closer together until the clips engage and compress the opposing walls of the organ together. The push tube 34 then can be withdrawn from the catheter and a cutting device can be advanced through the lumen 24C to sever the tails of the cords proximally of the cord lock to enable the tails of the cords to be removed. The clips are maintained in their tissue clamping configuration by engagement by the edge 44 (FIG. 9) of the cord lock 38 that prevents the cords from slipping back through the cord lock. Other self-locking devices, known in the art, may be employed for this purpose.

In a preferred embodiment the clips are formed so that when in their expanded configurations and when brought together in the absence of tissue, the legs of one of the clips will be interposed between and interdigitated with the legs of the other clip, as described more fully in pending U.S. patent application Ser. No. 15/906,763, filed Feb. 27, 2018, the disclosure of which is hereby incorporated by reference, in its entirety. To that end, the legs of each of the clips may be formed with an expanded configuration in which the legs of at least one and, preferably both clips define a conical locus so that when brought together, in the absence of tissue, the tips of the legs of each clip extend beyond the tips of the legs of the other clip. When tissue is present between the clips, the tissue can be constrained in a serpentine pattern that circumscribes the central axis of the clips.

In another embodiment the needles and the distal ends of their respective lumens can be parallel and the catheter may be steerable, so that it can be oriented, while under appropriate imaging, to aim its distal tip to selectively point one of the needles toward a wall of the atrial appendage. That needle then is advanced by its associated needle control tube to drive the needle through the appendage wall to locate the tip of the needle outside of the appendage wall. The associated clip push rod then can be advanced through the needle to deploy that clip externally of the appendage wall. That needle then can be withdrawn back into its catheter lumen and the catheter can be reoriented to direct the other needle toward the opposing wall of the appendage. That needle then can be advanced through the opposing wall of the appendage and its clip can be deployed externally of the opposing appendage wall. With the opposing walls of the hollow anatomical structure disposed between the deployed clips, the cord lock 38 then can be advanced over the cords and the procedure can be completed as described above.

Figure 20:
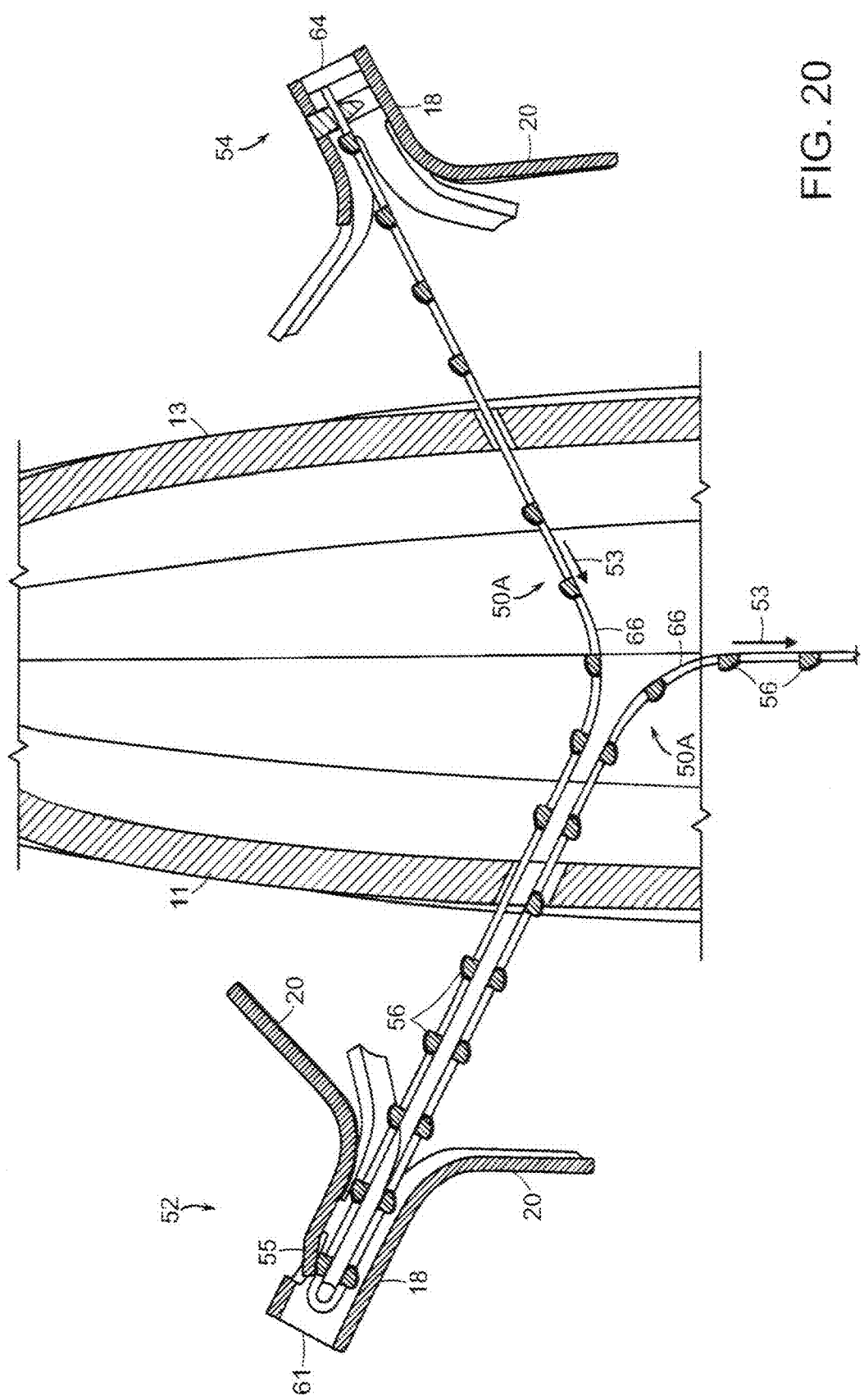
FIG. 20 is a diagrammatic illustration of another embodiment of the invention utilizing a single cord to connect the clips.
Figure 21:
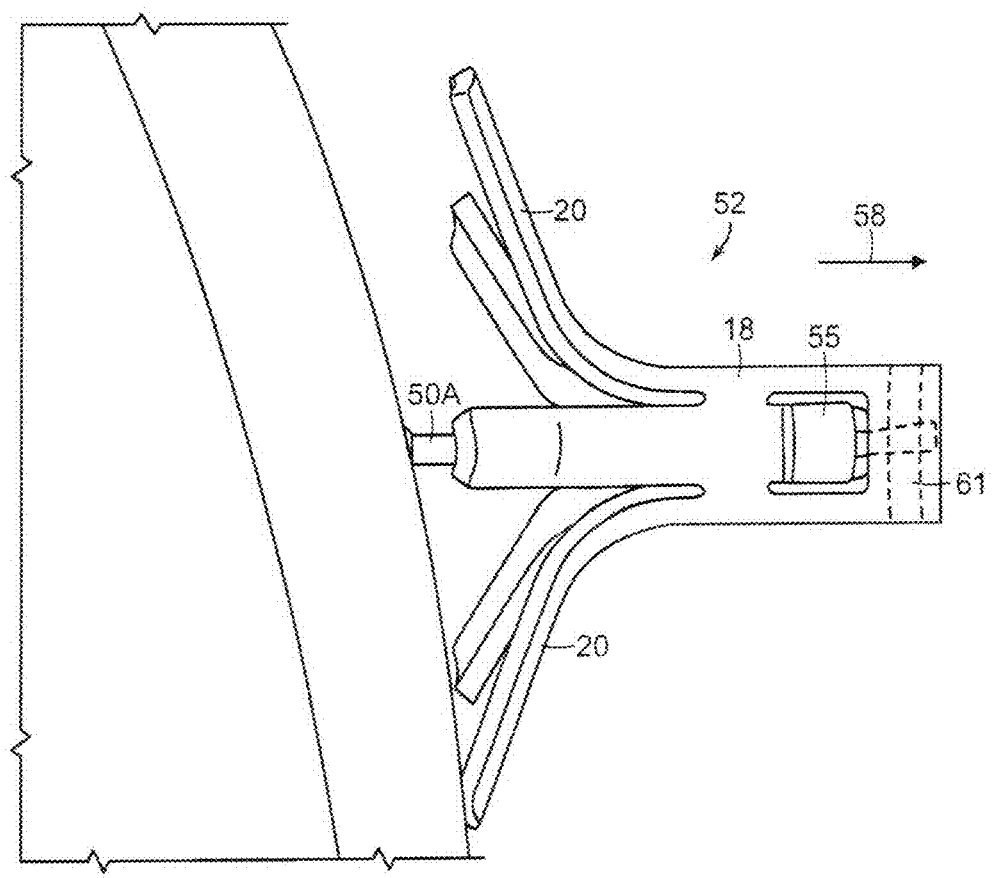
FIG. 21 is a side view of the first clip of the embodiment of FIG. 20.
Figure 22:
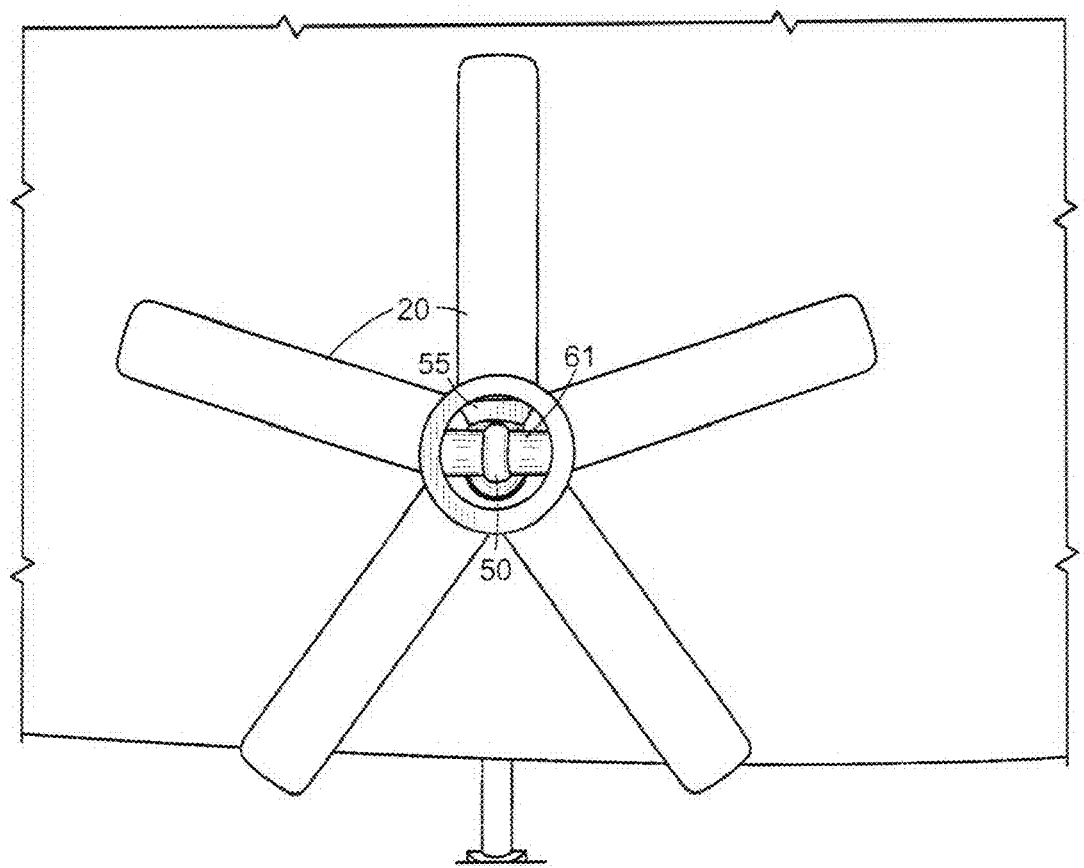
FIG. 22 is an end view of the first clip of the embodiment of FIG. 20 as seen from the tubular end of the clip.
Figure 23:
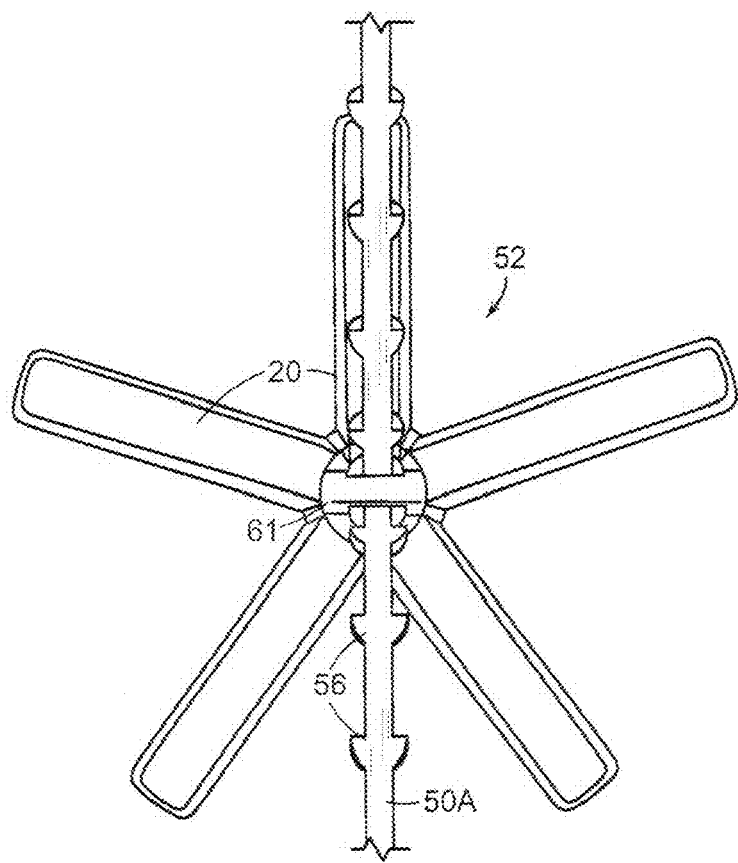
FIG. 23 is an end view of the first clip of the embodiment of FIG. 20 as seen from the leg end of the clip.
Figure 24:
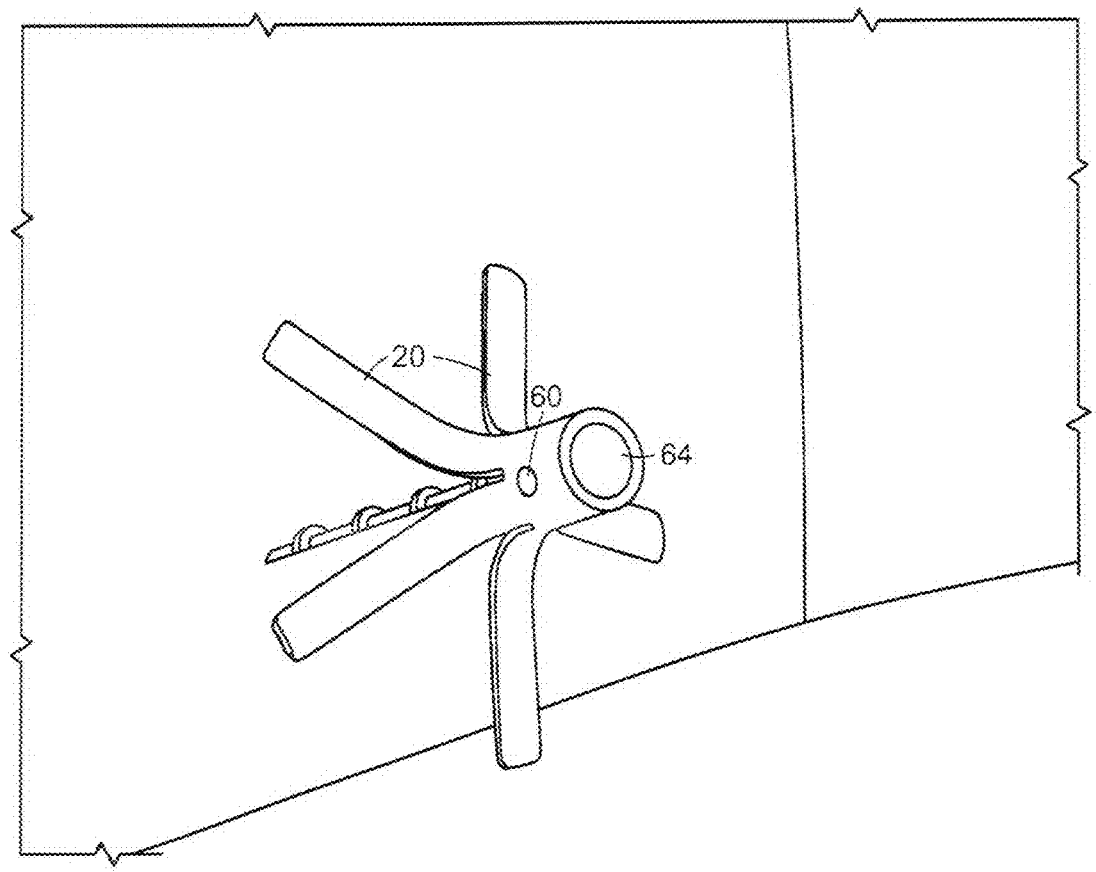
FIG. 24 is an isometric illustration of the second clip attached to an end of the cord.

FIG. 20 illustrates, schematically, another embodiment in which a single cord 50A is employed to connect the clips 52, 54 and draw them together. In this embodiment, the single cord 50A extends from the proximal end of the catheter, through the lumen 24C, through one of the slots 26 to and through a first clip 52 disposed in the lumen 24A. The first clip 52 and the cord 50A are constructed to enable the cord 50A to slide through the first clip 52 in one direction only, as suggested by the arrows 53 in FIG. 20. After passing through the first clip 52 the cord 50A exits the catheter lumen 24A, passing through the other slot 28 and is attached securely to the tubular body 18 of the second clip 54 that is contained in the other catheter lumen 24B. FIGS. 21-23 illustrate an embodiment of a first clip 52 having a tubular body 18 and legs 20 as in the embodiment first-described above. In this embodiment the body 18 of the first clip 52 is formed to have a locking tab 55 that projects slightly into the lumen of the tubular body 18 and toward the tubular end of the body 18. The cord 50A may be formed to have a plurality of bump-like protrusions 56 spaced along the length of the cord (FIGS. 23-27). The protrusions 56 are configured to cooperate with the locking tab 55 of the first clip 52 to allow the cord to pass through the clip 52 toward and through the end of the tubular body only in a direction indicated by the arrow 58 in FIG. 21. The first clip 52 also includes a pin 61 that extends diametrically of and is secured to the tubular body 18 between the locking tab 55 and the end of the tubular body 18. The cord 50A is configured to allow it to slide partially about the pin 61 to allow the cord to pass into the body 18, past the locking tab 55, about the pin and exit in a reverse direction. The cord 50A then extends to the second clip 60 to which it is securely and immovably attached. The end of the cord 50A is attached to the second clip 54, as by an enlarged portion 64 of the cord that is received in the tubular body 18 of the second clip and is held in place by a transverse pin 62 secured to the tubular body and passing through the enlarged portion 64.

Figure 25:
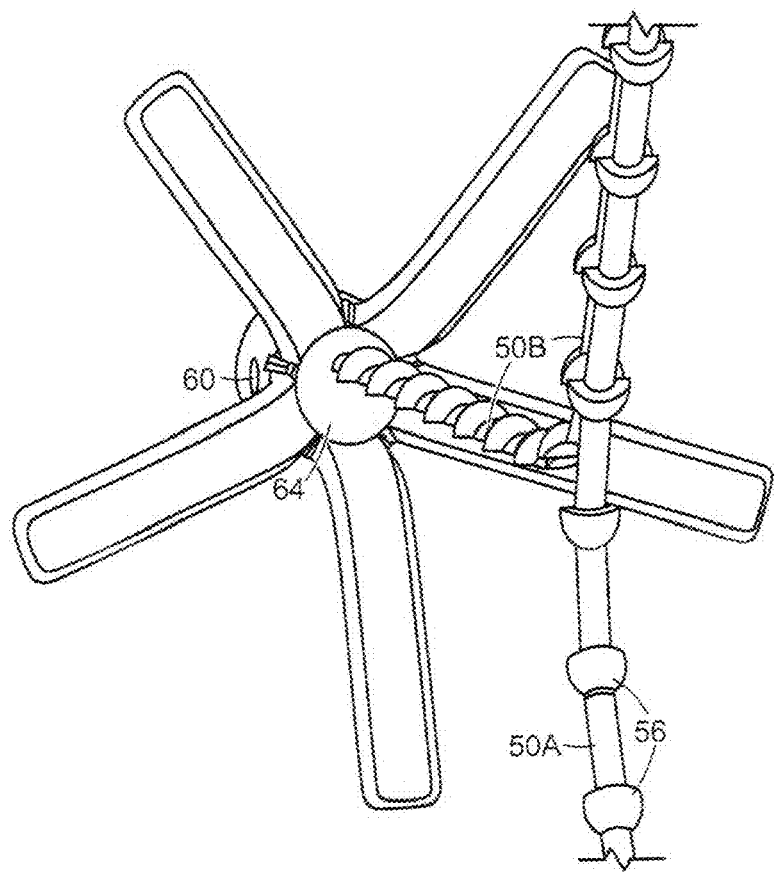
FIG. 25 is a diagrammatic isometric illustration of the second clip with the cord attached to the second clip.
Figure 26:
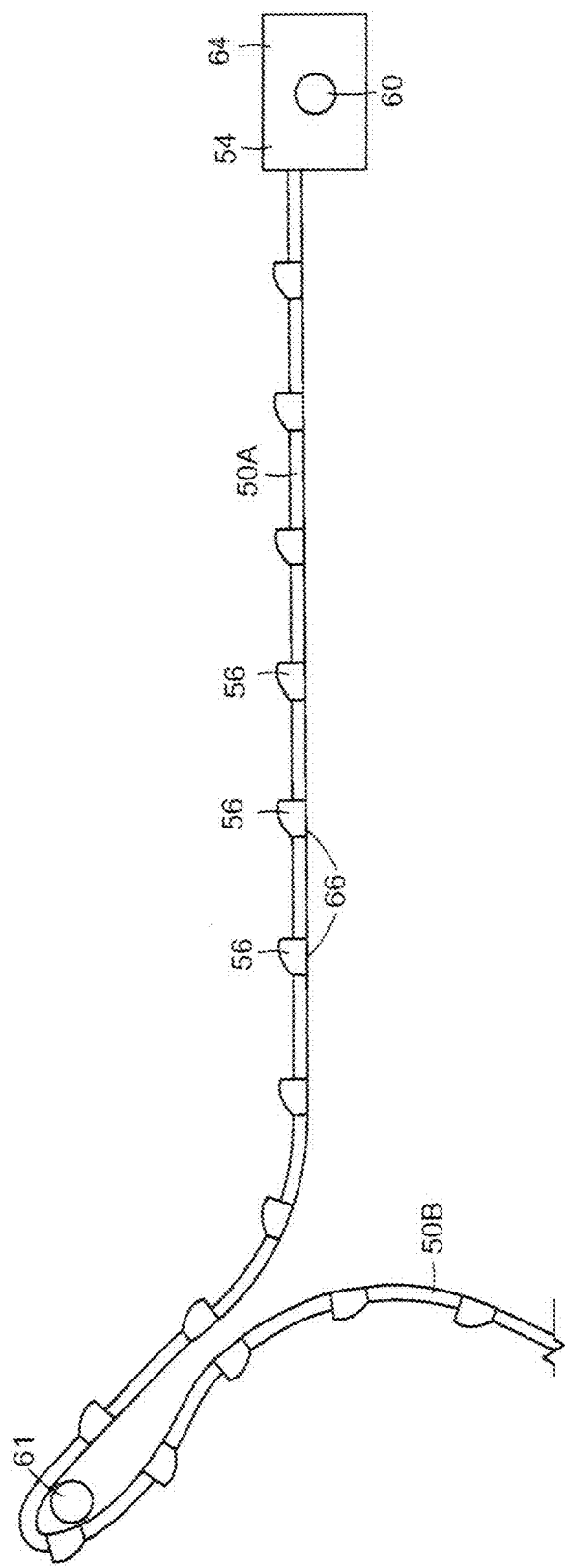
FIG. 26 is a diagrammatic side illustration of the cord, the tail of the cord and the second clip attached to the cord.

The cord 50A may be formed in a variety of ways, one of which is best illustrated in FIGS. 25 and 26, in which the cord may be injection molded to have a flat surface 66 that extends along the length of one side of the cord 50A with the protrusions 56 formed on the other side of the cord. The flat side 66 of the cord may face inwardly within the first clip 52 so that the flat, smooth side of the cord 50A slides easily against and about the pin 61 while the protrusions can engage the locking tab 55. It should be understood that other configurations for the cord and the manner that it engages with the first clip to limit movement of the first clip only toward the second clip may be employed.

In this embodiment, after the catheter has been navigated to the selected region of the hollow target anatomical structure, the needles are advanced to pierce the opposing walls of the structure, the then clips are ejected from the needles by the clip push rods to position the clips exteriorly of the structure with the opposing structure walls disposed between the deployed clips. The tail of the cord at the proximal end of the catheter then can be pulled, to draw the clips together to clamp the opposing walls of the organ together. A cutting instrument then can be advanced to sever the tail of the cord 50A to enable its removal as described above.

Figure 27A:
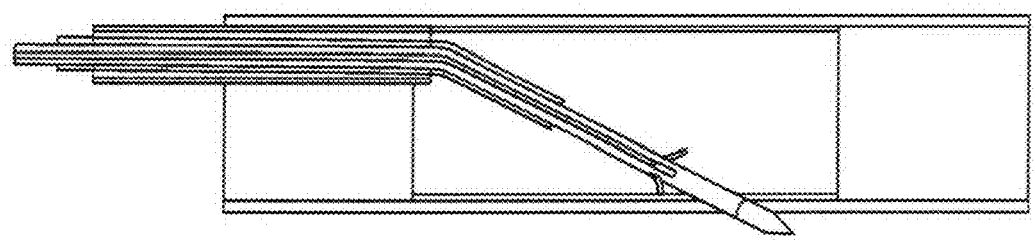
Figure 27B:
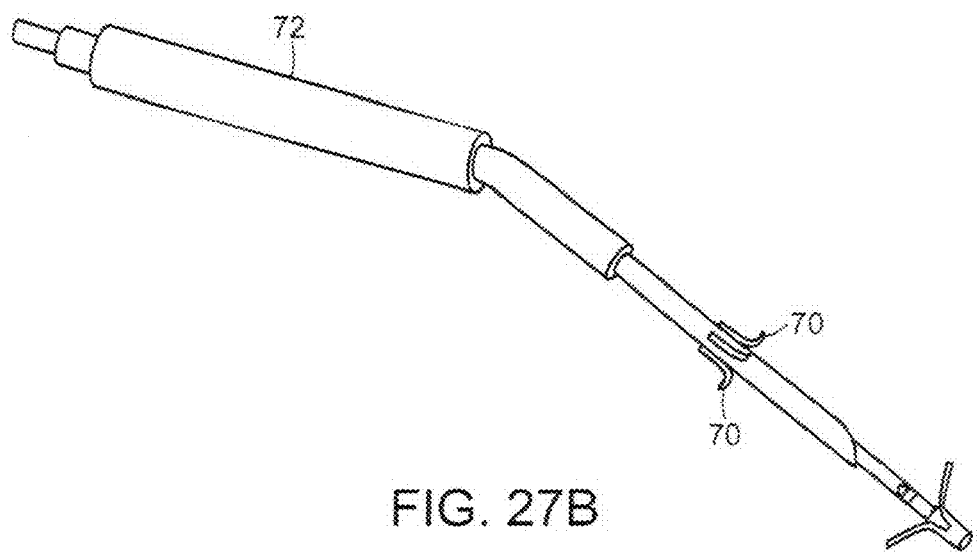

FIGS. 27(a) and 27(b) illustrate an embodiment where the needles piercing the wall of the hollow anatomical structure or organ includes a stop 70 to limit the travel of the sharp tip in a controlled manner from penetrating much beyond the wall thickness of the structure. In an embodiment of the invention, the needle contains a stop 70 that is normally covered by a sheath 72 that keeps the stop in a closed configuration. Prior to piercing the tissue, the sheath is retracted to enable the stop to self-deploy and then the needle is advanced to pierce the tissue. Following this, the occlusion clip is deployed. The stop may be formed from a superelastic material, such as Nitinol, so that it can lie flush and constrained against the outer surface of the needle by the retractable sheath 72. The stop may be adapted to resiliently spring to a radially projecting configuration upon retraction of the sheath. After the occlusion clip has been deployed, the sheath can be advanced over the stop to return it to its flush position.

FIG. 28 shows, diagrammatically, an embodiment of the invention where the needle or delivery device is delivered through the working channel of an endoscope and in which an embodiment of the invention may be guided to various deployment sites, utilizing the fiber optic imaging function of the endoscope.

Figure 29D:
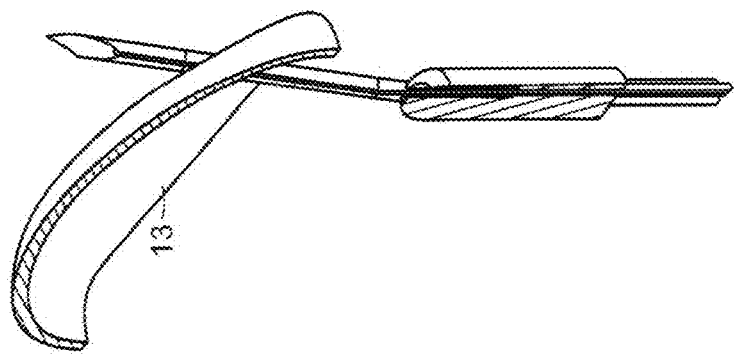
Figure 29C:
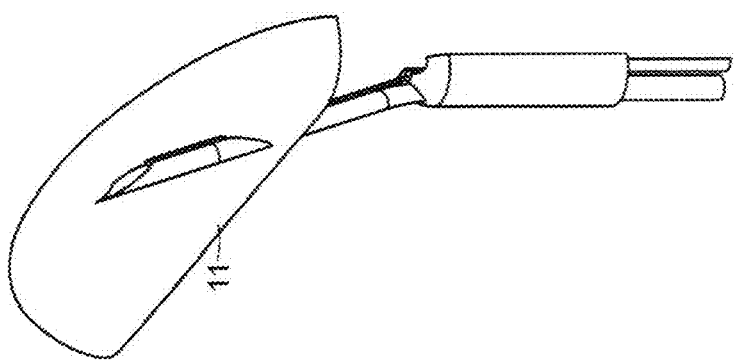
Figure 29B:
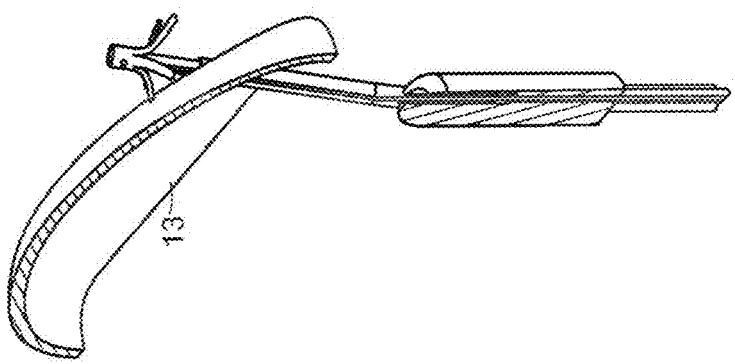
Figure 29A:
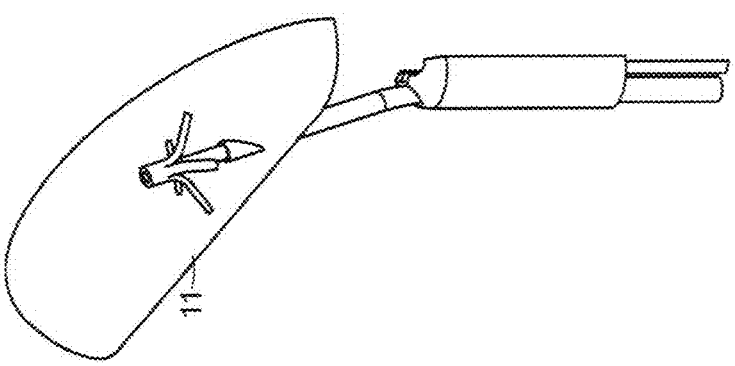

FIG. 29A-29D show the sequence of operations of a modified embodiment of the invention in which both occlusion clips are contained, in tandem, in a single needle. In this embodiment the catheter is navigated to orient the needle toward one wall of the hollow structure. The needle is advanced to pierce that wall and the clip is ejected by advancing a pusher tube that pushes both clips through the needle lumen, to release only the first of the clips externally of the structure (FIGS. 29A, 29B). Then the needle is retracted back into the catheter which is then reoriented to direct the needle at the other structure wall. The pusher then is advanced to eject the second clip out of the needle, deploying the second clip on the other side of the structure (FIGS. 29C, 29D). The needle is then retracted and the clips are pulled and locked together as described above.

FIG. 30 is a photograph of a portion of the outside of a stomach that has been endoluminally accessed and in which one of the clips has been deployed outside of the stomach.

FIG. 31 is a photograph of the exterior of a stomach that has been accessed endoluminally and in which three occlusion clips have been applied against the external surfaces of the stomach to draw the opposing stomach walls together to reduce the stomach volume. The clips, when secured together, compress the stomach walls so that no portion of the clips protrude above the outer surface of the stomach, preventing the clips from injuring surrounding tissue.

FIGS. 32a and 32b are photographs of a stomach that has been surgically opened to show the close approximation of the opposing walls of the stomach by the clips.

It should be understood that the foregoing description of the invention is intended merely to be illustrative thereof and that other embodiments, modifications and equivalents may be apparent to those skilled in the art without departing from the principles of the invention.

The invention claimed is:

1. Apparatus for endoluminally drawing opposing walls of a hollow mammalian anatomical structure toward each other, thereby to at least partly occlude the structure, the walls defining a lumen of the anatomical structure, the apparatus comprising:
a catheter having proximal and distal ends and advanceable through a natural body lumen to the hollow anatomical structure, the catheter having two catheter lumens open at the distal region of the catheter, each lumen containing a needle having an outlet, each needle containing an occlusion clip, each clip being configurable from a low-profile configuration containable within the needle to a deployed, configuration having larger dimensions when ejected from the needle;
the needles being extendable from the distal ends of their catheter lumens to pierce opposing walls of the anatomical structure and locate the needle outlets exteriorly of the anatomical structure;
a clip pusher associated with each occlusion clip and movable within its associated needle to push the clips out of the needle outlets while the distal tips of the needles are located exteriorly of the walls of the anatomical structure, thereby deploying the clips on opposite sides of the anatomical structure;
at least one cord connecting the clips and being manipulable to draw the clips toward each other after the clips have been ejected from the needles to draw the opposing walls of the anatomical structure toward each other between the clips; and
a locking member engageable with the at least one cord for securing the clips in a selected position.

2. The apparatus as defined in claim 1 wherein each clip is expandable from its low profile to its enlarged, deployed, profile after release from the needles.

3. The apparatus as defined in claim 2 wherein the clips are self-expandable upon ejection from the needles.

4. The apparatus as defined in claim 3 wherein each of the clips comprises a tubular body and a plurality of legs extending from the tubular body, the legs being resiliently self-expandable from the low-profile configuration to an expanded configuration in which the legs extend more radially outward from the tubular body.

5. The apparatus as defined in claim 4 further comprising:
the clips being configured so that, when the clips are brought together in the absence of tissue, the legs of the clips are interdigitated.

6. The apparatus as defined in claim 5 further comprising the legs of the clips having sufficient stiffness so that when tissue is clamped between the clips, the tissue is constrained in a serpentine configuration.

7. The apparatus as defined in claim 1 wherein each clip has a separate cord, each cord having a head end and a tail, and wherein the locking member comprises a self-securing cord-lock, the tails of the at least one cord passing through the cord lock, the at least one cord and cord lock being constructed to permit the at least one cord to move through the cord lock only in a direction that draws the clips toward each other.

8. The apparatus as defined in claim 7 further comprising:
the cord lock being a separate element;
the catheter having a third lumen for releasably containing the cord lock;
a pusher tube movably disposed in the third lumen and adapted to push the cordlock out of the third lumen, the tails of the cords extending through the cord lock and through the pusher tube.

9. The apparatus as defined in claim 7 wherein each clip has a tubular body and wherein the head end of each cord is attached to the tubular body of its associated clip with its tail extending through the leg end of the clip.

10. The apparatus as defined in claim 1 wherein there is a single cord, the single cord having a head and a tail, the tail passing slidably through a first of the clips and the head end being secured to a second of the clips, the single cord and the first clip cooperatively enabling the cord to pass through the first clip only in a direction to draw the clips together.

11. The apparatus as defined in claim 10 wherein the means for securing comprises
the cord having a plurality of projections formed along its length and extending only on one side of the cord, the opposite side of the cord being free of projections and being slidable against a surface of the first clip, the tubular portion of the clip having a detent extending into the tubular body in a position to engage the projections to enable the projections to move past the detent only in a direction to draw the clips toward each other.

12. The apparatus as defined in claim 1 wherein the needles are oriented in the catheter in a diverging orientation.

13. The apparatus as defined in claim 1 wherein the needles are oriented in the catheter in parallel.

14. The apparatus as defined in claim 1 wherein the distal end of the catheter is steerable.

15. A method for endoluminally occluding a hollow anatomical structure comprising:
advancing, endoluminally, a first needle carrying a first self-expandable occlusion clip and a first cord connected to the first clip, to the anatomical structure;
advancing, endoluminally, a second needle carrying a second self-expandable occlusion clip and a second cord connected to the second clip, to the anatomical structure;
causing the needles to pierce the walls of the anatomical structure at opposing locations and, while so positioned, ejecting the clips from their respective needles to position the clips externally of the structure whereby the clips can self-expand externally of the anatomical structure;
drawing the clips together by manipulating their cords to draw the opposing walls of the structure toward each other to an at least partially occluding configuration; and
applying a locking member to the cords to secure the clips in their at least partially occluding configuration.

16. A method for endoluminally occluding a hollow anatomical structure comprising:
advancing, endoluminally, to the anatomical structure, a hollow needle having an outlet, the needle carrying a first occlusion clip and a second occlusion clip, the clips being contained in tandem within the needle, each of the clips being self-expandable from a low profile containable in the needle to an enlarged dimension when ejected from the needle, a flexible cord being attached to the second clip and extending, slidably, through the first clip, the cord and first clip being cooperatively constructed to permit the cord to pass through the first clip only in a direction that draws the clips toward each other;
causing the needle to pierce a wall of the anatomical structure at a first location to locate the needle outlet exteriorly of the anatomical structure;
ejecting the first clip from the needle to locate the clip exteriorly of the structure;
retracting the needle into the anatomical structure and then causing the needle to pierce the wall of the structure at a second location spaced from the first location to locate the needle outlet exteriorly of the structure and then ejecting the second clip from needle to locate the second clip exteriorly of the structure at a circumferentially spaced location from the first clip whereby both clips are positioned at circumferentially spaced locations externally of the anatomical structure whereby the clips can self-expand to their enlarged profiles externally of the anatomical structure;
drawing the cord through the first clip to draw the clips together to draw the opposing walls of the structure toward each other to an at least partially occluding configuration; and
whereby the relative positions of the clips are locked in their at least partially occluding configuration by cooperation of the cord and first clip.

17. The method as defined in claim 16 wherein the cooperative structure of the cord and the first clip comprises:
the cord having a plurality of longitudinally spaced projections formed along the cord, the first clip having a detent enabling the projections to pass through the first clip only in a direction that draws the clips toward each other.

18. Apparatus for endoluminally drawing opposing walls of a hollow mammalian anatomical structure toward each other, thereby to at least partly occlude the structure, the walls defining a lumen of the anatomical structure, the apparatus comprising
an intraluminally advanceable catheter having a hollow needle with an outlet, the needle carrying a first occlusion clip and a second occlusion clip, the clips being contained in tandem within the needle in readiness to be ejected serially from the needle, the catheter being manipulable to direct the needle in different radial directions, whereby the needle can be directed to pierce the structure walls to locate the outlet at opposed locations externally of the structure;
each of the clips being self-expandable from a low profile containable in the needle to an enlarged profile when ejected from the needle whereby the clips may be deployed externally of the structure;
a flexible cord attached to the second clip and extending, slidably, through the first clip, the cord and first clip being cooperatively constructed to permit the cord to pass through the first clip only in a direction that draws the clips toward each other and prevents reversal;
whereby the relative positions of the deployed clips may be drawn together to at least partially occlude the lumen of the structure and be locked in their at least partially occluding configuration by cooperation of the cord and first clip.

* * * * *